United States Patent
Puckett et al.

(10) Patent No.: US 6,826,973 B2
(45) Date of Patent: Dec. 7, 2004

(54) HEATED MECHANICAL ARM

(75) Inventors: Nancy H. Puckett, Roswell, GA (US); Audra S. Wright, Woodstock, GA (US); Martha L. Tate, Atlanta, GA (US); Jason C. Cohen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 85 days.

(21) Appl. No.: 10/324,834

(22) Filed: Dec. 20, 2002

(65) Prior Publication Data

US 2004/0118228 A1 Jun. 24, 2004

(51) Int. Cl.[7] ............................................. G01M 19/00
(52) U.S. Cl. .......................................... 73/866.4; 73/73
(58) Field of Search ..................... 73/73, 866.4; 223/70

(56) References Cited

U.S. PATENT DOCUMENTS

| | | | |
|---|---|---|---|
| 1,561,285 A | | 11/1925 | Sesler |
| 2,545,281 A | | 3/1951 | Hunt |
| 3,341,394 A | | 9/1967 | Kinney |
| 3,502,538 A | | 3/1970 | Peterson |
| 3,502,763 A | | 3/1970 | Hartmann |
| 3,542,615 A | | 11/1970 | Dobo et al. |
| 3,789,518 A | * | 2/1974 | Chase ........................ 434/272 |
| 3,952,584 A | | 4/1976 | Lichstein |
| 4,041,203 A | | 8/1977 | Brock et al. |
| 4,257,188 A | | 3/1981 | Barker |
| 4,340,563 A | | 7/1982 | Appel et al. |
| 4,357,827 A | | 11/1982 | McConnell |
| 4,720,415 A | | 1/1988 | Vander Wielen et al. |
| 4,932,919 A | | 6/1990 | Shapero |
| 5,018,977 A | * | 5/1991 | Wiley et al. ................. 434/274 |
| 5,066,259 A | | 11/1991 | Acker |
| 5,067,924 A | | 11/1991 | Munter |
| 5,361,627 A | | 11/1994 | Levesque |
| 5,397,237 A | * | 3/1995 | Dhont et al. ................. 434/262 |
| 5,419,729 A | | 5/1995 | Gross |
| 5,425,265 A | | 6/1995 | Jaisinghani |
| 5,492,943 A | * | 2/1996 | Stempel ....................... 523/111 |
| 5,518,436 A | | 5/1996 | Lund et al. |
| 5,913,708 A | | 6/1999 | Gross |
| 5,979,235 A | * | 11/1999 | Kurz et al. ................. 73/432.1 |
| 6,015,935 A | | 1/2000 | LaVon et al. |
| 6,107,537 A | | 8/2000 | Elder et al. |
| 6,152,906 A | | 11/2000 | Faulks et al. |
| 6,220,088 B1 | * | 4/2001 | Scales et al. ................. 73/172 |
| 6,234,804 B1 | * | 5/2001 | Yong ......................... 434/267 |
| 6,298,714 B1 | | 10/2001 | Courtray |
| 6,413,142 B1 | | 7/2002 | Weastler |
| 6,446,495 B1 | * | 9/2002 | Herrlein et al. ................. 73/73 |
| 6,464,557 B1 | | 10/2002 | Ohba et al. |
| 6,503,525 B1 | | 1/2003 | Paul et al. |
| 6,534,074 B2 | | 3/2003 | Krzysik et al. |
| 6,543,657 B2 | * | 4/2003 | Fan et al. ..................... 223/66 |
| 6,557,398 B2 | | 5/2003 | Lindmark et al. |
| 2002/0127520 A1 | * | 9/2002 | Grace et al. ................. 434/100 |
| 2002/0172214 A1 | * | 11/2002 | Grantham .................... 370/431 |
| 2002/0191669 A1 | | 12/2002 | Fan et al. |

FOREIGN PATENT DOCUMENTS

| | | | | |
|---|---|---|---|---|
| GB | 2272182 A | | 5/1994 | |
| JP | 06020963 A | * | 1/1994 | ......... H01L/21/205 |

OTHER PUBLICATIONS

U.S. Application No. 10/324,884, filed Dec. 20, 2002.
U.S. Application No. 10/324,605, filed Dec. 20, 2002.
U.S. Application No. 10/324,365, filed Dec. 20, 2002.

* cited by examiner

*Primary Examiner*—Charles D. Garber
(74) *Attorney, Agent, or Firm*—Dority & Manning, P.A.

(57) ABSTRACT

An evaluation apparatus is provided for pre-screening a material for use in an absorbent article. The evaluation apparatus includes a simulated body part having a simulated skin substrate. The material is placed on or near the simulated skin substrate, and a predetermined amount of simulated physiological fluid is insulted into the material at a pre-measured location. After a predetermined time, the simulated skin substrate is removed from the body part and fluid loss measurements are taken.

31 Claims, 5 Drawing Sheets

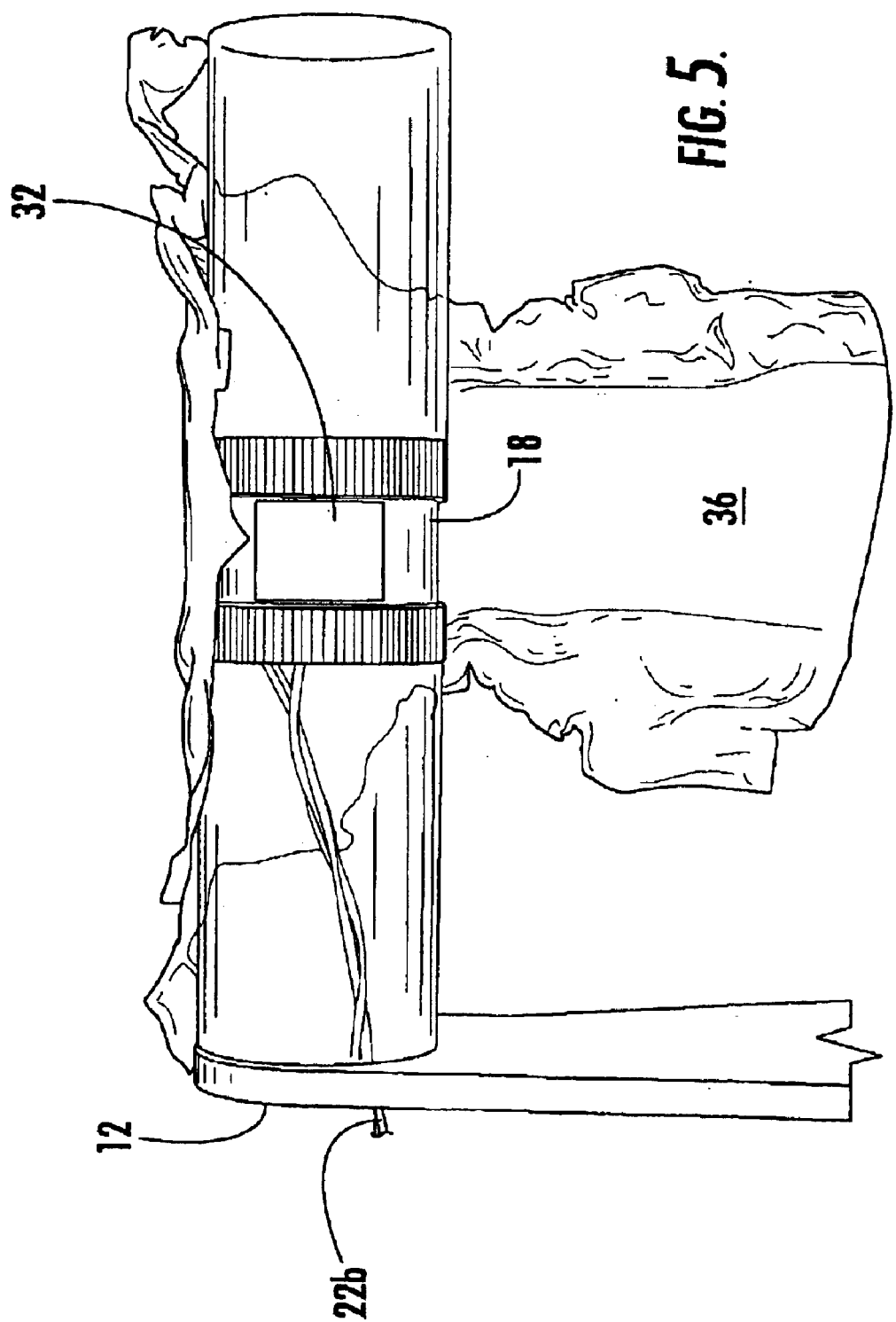

HEATED MECHANICAL ARM

BACKGROUND OF THE INVENTION

Absorbent articles such as diapers, adult incontinence garments, feminine care products, child training pants, pull-ups, bandages, gloves and similar products that directly contact skin are well known. A disposable absorbent article is typically composed of a top layer that is adjacent to a user's body and a back layer that faces the clothing of the user. An absorbent material is located between the top layer and the bottom layer. The top layer permits a liquid from the user to move through the top layer toward the back layer. The back layer does not allow liquid to be transferred from the inside of the absorbent article onto the user's clothing. The absorbent material absorbs the liquid and keeps the skin dry.

During normal operation after a fluid is discharged from a user, the fluid will flow through the top layer and be absorbed by the absorbent material. The absorbent material is designed to absorb, redistribute, and store the fluid until the absorbent article is discarded. In some instances, however, fluid may return from the absorbent material to once again contact the user's skin. Fluid return can occur, for example, if the absorbent material cannot sufficiently absorb the fluid due to the composition of the absorbent material. Unabsorbed liquid undesirably results in over-hydration of the contacted skin and in turn, increases a chance of skin irritation to the user. In addition to being an irritant, excessive moisture on the user's skin can cause, among other things, the growth of microorganisms that can lead to the onset of rashes or infection.

Various tests exist for measuring performance and suitability of absorbent materials to prevent the foregoing problems. Known tests include capacitance, conductance, electrical impedance, and/or evaporative or Trans-Epidermal Water Loss (TEWL) evaluations. Typically, these tests measure fluid absorbency, fluid leakage, and other criteria of the materials for use in absorbent articles.

One such test is the Adult Forearm Test or "armband" test, which is conventionally used to evaluate the effectiveness of disposable diapers to keep the skin dry. One variation of the armband test uses pre-loaded patches from diapers placed on an adult volar forearm. Changes in skin surface hydration are measured by evaporimetry or TEWL evaluation. Differences in skin surface hydration between cloth diapers and disposable paper diapers have been noted using this armband test variant.

Another armband test uses an intact diaper wrapped around the forearm. Physiological saline is injected into the diaper at a rate and volume that represent normal urination by a child. Post-occlusion measurements are made after one hour, and measurements of skin hydration are made by computerized evaporimetry or by electrical conductance.

BRIEF SUMMARY OF THE INVENTION

In general, the present invention provides an evaluation apparatus to evaluate materials quickly, efficiently and cost effectively. The evaluation apparatus acts as a pre-screening tool to bench test materials for diaper, childcare, feminine care, adult care, health care, competitive and other products without human subjects. The component parts of the invention are simple, reliable, and economical to manufacture and use. Also, used herein, the terms "simulated," "virtual," "artificial," "synthetic" and like terms are used interchangeably to indicate manufactured materials or objects, and in the case of substrates, dissected or bioengineered skin samples, unless otherwise indicated.

In one aspect of the invention, a heated mechanical arm includes a Plexiglas®-type cylinder, which simulates an adult forearm. The heated mechanical arm is designed to rapidly pre-screen and rank a material for further evaluation, possibly on human subjects. The heated mechanical arm further includes a fluid injection port and incorporates a heater element or a flexible heater. The flexible heater is made, for instance, from rubber silicone and can be wrapped about the mechanical arm. The heater includes a heater hole that complements the fluid injection port of the mechanical arm to simulate a sweat gland, pore, a urethra and the like.

Also in the foregoing aspect, a simulated skin substrate is placed on or near the heater. The heater heats the simulated skin to emulate normal human skin temperature. The material is wrapped about the skin and heater and insulted with saline or other simulated physiological fluid via the fluid injection port, either automatically or manually by a fluid loading device. At a predetermined time, the material is removed and the simulated skin is evaluated for dryness.

Thus, the present invention enables rapid pre-screening of materials by using economical artificial components and avoiding variables in a population of human subjects. Other aspects and advantages of the invention will be apparent from the following description and the attached drawings, or can be learned through practice of the invention.

BRIEF DESCRIPTION OF THE DRAWINGS

The above and other aspects and advantages of the present invention are apparent from the detailed description below and in combination with the drawings in which:

FIG. 5 is a perspective view of the simulated skin and a material attached to the heated mechanical arm.

Figure 1:
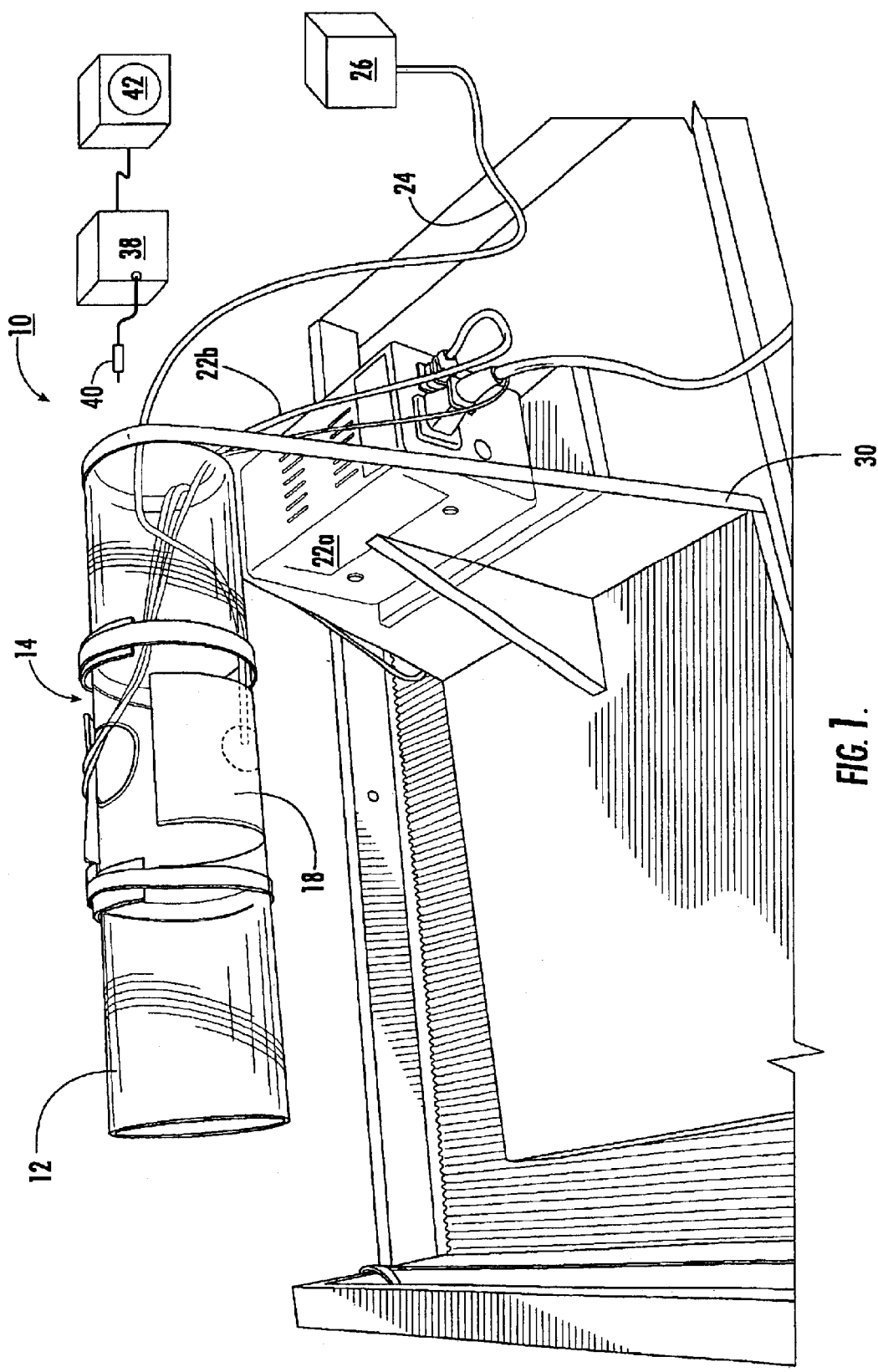
FIG. 1 is a perspective view of an apparatus in accordance with an aspect of the invention.

Repeat use of reference characters in the drawings and the detailed description is intended to represent same or analogous features or elements of the invention.

DETAILED DESCRIPTION OF THE DRAWINGS

Detailed reference will now be made to the drawings in which examples embodying the present invention are shown. The drawings and detailed description provide a full and detailed written description of the invention and the manner and process of making and using it, so as to enable one skilled in the pertinent art to make and use it. The drawings and detailed description also provide the best mode of carrying out the invention. However, the examples set forth herein are provided by way of explanation of the invention and are not meant as limitations of the invention. The present invention thus includes modifications and variations of the following examples as come within the scope of the appended Claims and their equivalents.

In general, the present invention is directed to an evaluation apparatus for quickly pre-screening and ranking products or materials without requiring human subjects. Once the materials are pre-screened or bench tested, a determination can be made as to which materials warrant additional testing and evaluation, possibly on human subjects. Materials may include an absorbent material, disposable or non-disposable diapers, diaper systems, adult incontinence products, feminine products, nursing healthcare products, child training products, bandages, gloves, face masks, and non-disposable products that contact a consumer's skin. Additionally, the material can be a nonwoven polymer material, an airlaid material, a wet material, a dry material, a treated material, and disposable or non-disposable materials.

As broadly embodied in FIGS. 1–5, an evaluation apparatus 10 includes an object or arm 12 with a heater 18 attached to the arm 12 and an artificial (simulated) skin 32 attached to the heater 18. A material 36 is disposed about the skin 32, and a pump or fluid delivery device 26 is provided to insult the material 36 with a simulated physiological fluid 28 via the arm 12 and heater 18. The fluid 28 may be water, saline, simulated menses fluid, simulated urine, artificial breast milk, blood, simulated blood, a solution of 0.9% sodium chloride, a colored solution, an exudate or any suitable material for simulating human body fluids. The foregoing components facilitate skin dryness measurements, which can be conducted by capacitance, conductance, electrical impedance, Trans-Epidermal Water Loss (TEWL), and other evaluations to measure skin hydration and moisturization. Material evaluators are thus able to rapidly pre-screen materials without the need for human subjects. Further details of the evaluation apparatus 10 and its operation are discussed below.

Referring to FIG. 1, there is shown a perspective view of one embodiment of the evaluation apparatus 10 in which the arm 12 is attached to a base 30. The arm 12 can be adjustably attached to the base 30 to facilitate the TEWL measurements that are described below. In this example, the arm 12 is formed of a Plexiglas® material and is approximately 3¼ inches×13⅝ inches with a 10¼ inch circumference to simulate an adult female forearm. Although the exemplary arm 12 is made of Plexiglas®, other materials such as acetyl plastic, an acrylic plastic, an elastomeric material, a high density polyethelene, a polymer, a metal, a glass, a composite material or similar moldable materials may be suitably used. Also, while the illustrated arm 12 is representative of a female forearm, it is not intended as a limitation of the invention. For example, the circumference of the arm 12 can be from about 3 inches to about 80 inches. Furthermore, the arm 12 can be formed alternatively as a lower torso mannequin, an upper-torso mannequin, a full-body mannequin, a mannequin hand, a mannequin leg, a mannequin foot, a mannequin head or other simulated body parts. Thus, it is to be understood that other simulated anatomical parts representing, for instance, a man, woman, child, infant, or animal having other than the illustrated cylindrical shape are within the scope of the invention.

FIG. 1 further shows the heater 18, briefly introduced above, wrapped around an attachment area 14 of the arm 12. The heater 18 is attached by any suitable device such as adhesive tape, hook and loop fasteners, hooks, buttons, snaps, pins, zippers, or the like to the arm 12.

As shown, the heater 18 can be fashioned from a flexible silicone rubber, neoprene, or other flexible material and is designed for removable attachment to the apparatus 10. The heater 18 in one aspect is a substantially liquid-proof or liquid-resistant body so that the fluid 28 can be insulted into the material 36, which is wrapped about the heater 18. Due to the liquid-proof nature of the heater 18, the fluid 28 does not adversely affect the heater 18 when the fluid 28 contacts it. A heater suitable for use with the exemplary arm 12 is a 3-inch×8⅛ inch rubber silicone Watlow 120 Volt (V) heater available from Watlow Electric Manufacturing Company of St. Louis, Mo. Other comparable heaters from other manufacturers may also be used for heater 18. It should also be understood that the heater 18 may be integrally formed, for instance, as heater elements within the evaluation apparatus 10 and is not limited to the illustrated wrappable heater 18. More specifically, in an alternative aspect of the invention, the arm 12 can be formed of a heatable silicone rubber in which a network of heating elements is embedded in the silicone rubber in order to simulate human skin temperature on a heating surface of the apparatus 10.

Heating the skin 32 with the heater 18 correlates the present invention to the conventional Adult Forearm Test in order to better support, for instance, advertising claims, and develop products. To simulate normal human skin temperature, the heater 18 is connected to a power source 22a via an electrical connection 22b as shown in FIG. 1. Heating elements (not shown) within the heater 18 can be heated from about 70° Fahrenheit (F.) to about 120° F., but are normally programmed or set at about 95° F. to emulate a surface temperature of normal human skin. The heater 18 can be controlled by an internal or external controller (not shown), which can set the temperature by rotary dials, switches, rheostats, or other analog or digital devices. Temperature controllers are known and need not be further described to understand this aspect of the invention.

Laboratory experiments have shown that TEWL measurements differ significantly when the skin 32 is heated to about 85–99° F. versus when the skin 32 is substantially at ambient laboratory temperature. By way of example, when the skin 32 is approximately 72° F. (ambient room temperature), TEWL is measured at approximately 10 g/m$^2$/hr. In contrast, when the skin 32 is heated by the heater 18 to about 95° F., TEWL measurements are 30 g/m$^2$/hr. Further details of the operation of the heater 18 and resulting TEWL measurements are provided below in Exemplary Procedures and Exemplary Results.

In one aspect of the invention, the fluid delivery device 26 of FIG. 1 may be a digital pump or a computer controlled pump, which delivers a predetermined amount of fluid 28 (see FIG. 3) through the arm 12. Although other pumps are available, a Masterflex® Computerized Water Pump, available from Cole-Parmer of Vernon Hills, Ill., is a suitable fluid delivery device 26. The Cole-Parmer Masterflex® Computerized Water Pump can be operated via a Windows® Linkable Instrument Network (WINLIN) software program to link multiple pumps and mixers in synchronized or unsynchronized sequences of operation. The WINLIN program also features:

Flow calibration by volume, weight or flow reference

Multiple flow, volume and torque units

Volumetrical or gravimetrical dispensing

Constant or ramped flow/speed control

A fluid tube 24 (alternatively, tubing or conduit herein) is also shown in FIG. 1 for delivering the simulated physiological fluid 28 through a heater hole 20 (see FIG. 3) in the heater 18. The heater hole 20 may be from about 0.25 inches to about 1 inch. The fluid tube 24 has a complementary outer diameter (OD) of between 0.2 inches to about 0.8 inches. In this exemplary arrangement, the tube 24 is routed within the apparatus 10 to ensure, for instance, that the tube 24 is not disturbed by external forces. However, it is to be noted that the tube 24 can be arranged externally to the apparatus 10 without affecting its operation. The operation of the tube 24 is described in greater detail below.

FIG. 1 further shows a measuring device 38 with a stand-mounted or hand-held probe 40 that can be used to determine skin dryness, diaper pooling, skin saturation and the like by evaluating the skin 32 after insulting the material 36 with the fluid 28. By way of example, a DermaLab® Trans Epidermal Water Loss (TEWL) probe, developed by Cortex Technology, Denmark, available from cyberDERM, Inc., Media, Pa., is a suitable measuring device 38, although any comparable probe may be used. An electronic display unit or monitor 42 can be electronically attached to the measuring device 38 to display the TEWL measurements. The measuring device 38 and/or monitor 42 can include a recording capability to automatically save TEWL or other measurements such as capacitance, conductance, or impedance to a magnetic tape, computer hard drive, disc or the like. Further details of the testing protocol and operation of the apparatus 10 and the measuring device 38 are discussed below.

Figure 2:
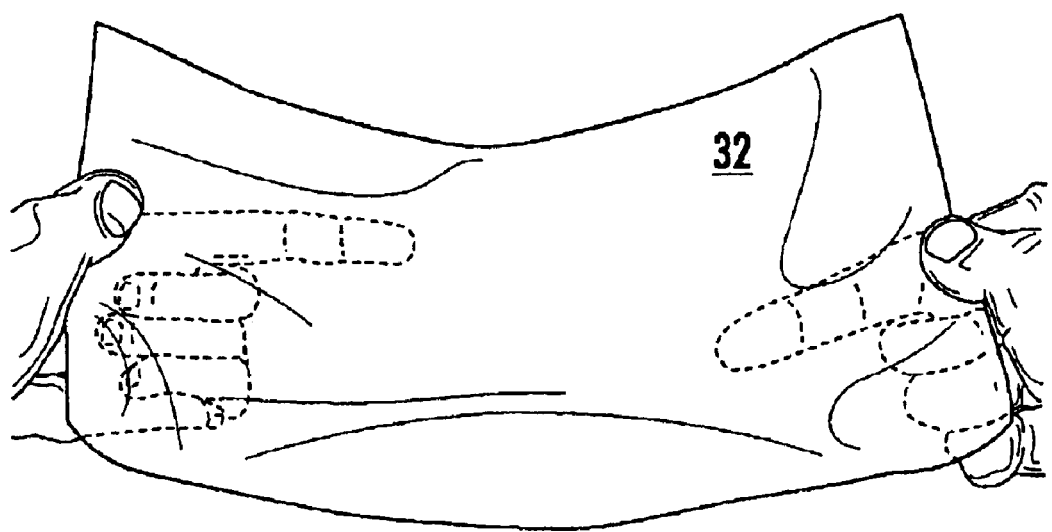
FIG. 2 is a perspective view of a portion of simulated skin in accordance with another aspect of the invention.

Referring to FIG. 2, a portion of the simulated skin 32 is shown. As introduced, after the material 36 is insulted with the fluid 28, the simulated skin 32, which is at least partially covered with the insulted material 36, is evaluated for wetness/dryness (TEWL) using the probe 40 of the measuring device 38 to prescreen the material 36.

A variety of simulated skin materials and products are suitable for use as simulated skin 32 to demonstrate the hydration and/or moisturization properties of personal care products, diapers and the like. Examples include but are not limited to VITRO-SKIN™ and VITRO-CORNEUM® available from IMS Inc., Milford, Conn.; TEST SKIN™ II from Organogenesis Inc., Canton, Mass.; SKINETHIC® from Skinethic Tissue Culture Laboratories, Nice, France; EpiDerm™ simulated human skin from MatTek Corporation, Ashland, Mass.; a medical grade collagen film; a collagen in a sausage casing; cellulose film; a custom prepared chamois available from Acme Sponge and Chamois Company, Tarpon Springs, Fla.; a cultured or bioengineered skin substrate; a living/preserved skin sample from animal models such as but not limited to a pig, a monkey and a human cadaver; and similar materials.

By way of example, VITRO-SKIN™ substrate contains protein and lipid components and is designed to have topography, pH, critical surface tension and ionic strength that mimic human skin. Its consistent topography ("N-19 topography") and wetting properties across each sheet of VITRO-SKIN™ are optimized to mimic relatively smooth skin found on the human back. Thus, testing done on VITRO-SKIN™ is generally more reproducible than that performed on variable human skin samples due to the consistent topography of VITRO-SKIN™. In comparison, VITRO-CORNEUM® is a collagen-based substrate with properties similar to human stratum corneum. VITRO-CORNEUM® substrate is designed to simulate the thickness, visco-elasticity and surface properties of human stratum corneum; i.e., the outer layer of epidermis of primarily dead skin cells. The EpiDerm™ bioengineered human skin incorporates stratified epidermal layers, including a functional stratum corneum.

Another suitable simulated skin substrate is collagen in a sausage casing, Collagen is a cost-effective alternative for pre-screening materials 36 since collagen does not have to be handled and stored as a biological sample. An exemplary collagen is available from NATURIN GmbH, Weinhein, Germany, under the designation of COFF12224. COFF12224 is a collagen film having a basis weight of about 28 g/m$^2$. Another exemplary collagen film is available from Devro, Inc, Geneva, Ill., under the designation of Cutisin™.

Figure 3:
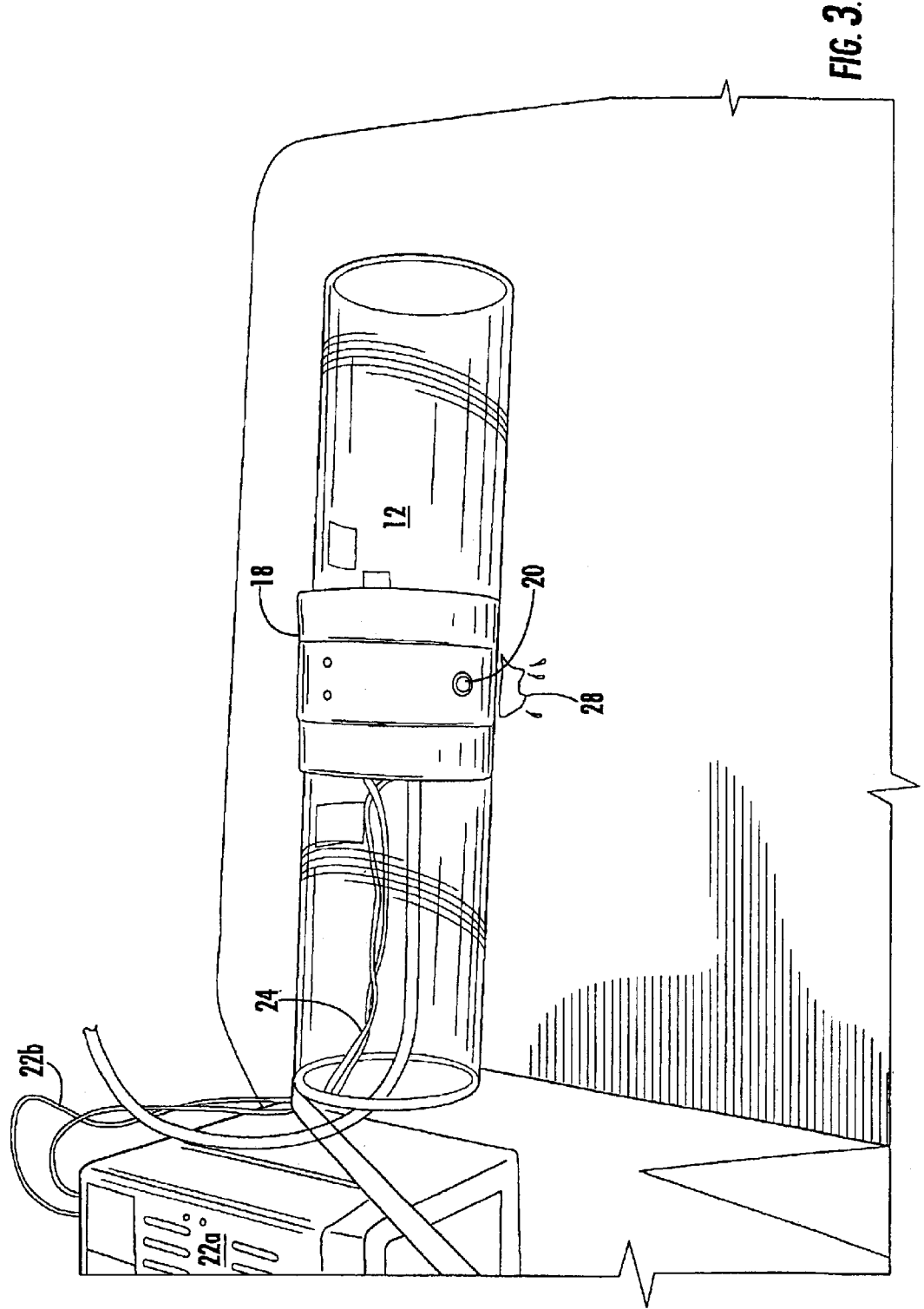
FIG. 3 is a perspective view of a heater hole as used with a heated mechanical arm in accordance with a further aspect of the invention.

With reference to FIG. 3, a heater hole 20 is shown in this perspective view of heater 18, which is wrapped about the arm 12. In this aspect of the invention, the heater hole 20 is 5/16 inch to simulate a normal urine load of a child. However, a plurality of heater holes 20 having various other sizes may be utilized to simulate a variety of human age groups and bodily functions. Also, as noted above, the arm 12 may also be other shapes or anatomical parts such as a thigh, an upper arm and the like, and is not limited to the simulated, cylindrically shaped forearm as shown. For instance, a large size adult under garment is approximately 33 inches in length and the arm 12 would have an accommodating 30 inch circumference. Thus, the removable heater 18 can be sized to match any other simulated body part such as an infant's torso and may include one or more heater holes 20 of various sizes.

Figure 4:
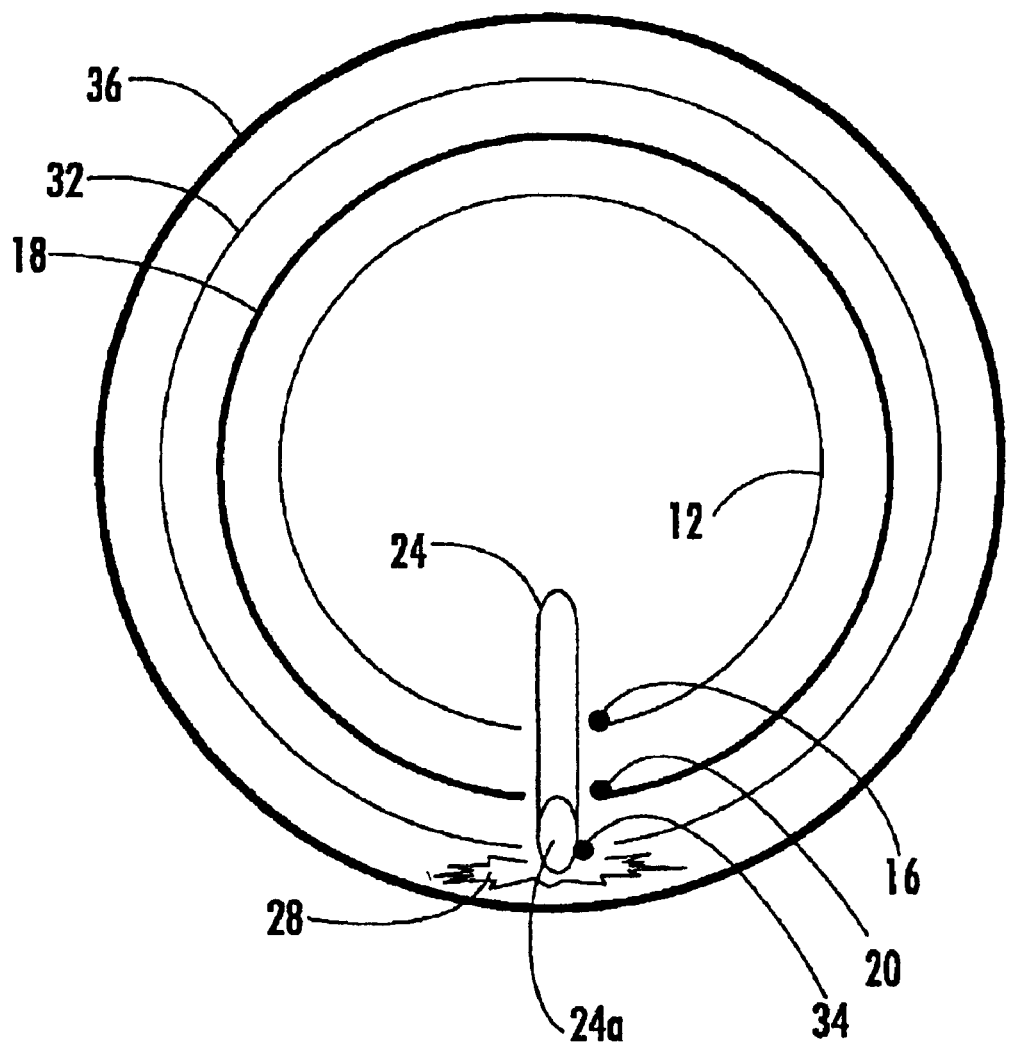
FIG. 4 is an end view of the heated mechanical arm particularly showing a fluid injection port and the heater hole in accordance with another aspect of the invention.

FIG. 4 shows the heater 18 attached in the attachment area 14 of the arm 12 as previously discussed (see FIG. 1). A fluid injection port 16 is shown in the arm 12 through which the fluid tube 24 is inserted. In this example, the fluid injection port 16 is about 0.25 inches but may be up to about 0.5 inches in circumference. The fluid tube 24 is also at least partially inserted through the heater hole 20, which in this example is substantially aligned with the fluid injection port 16. Also seen in FIG. 4, the simulated skin 32 is attached to the heater 18 to be heated to the previously described human skin temperature.

With further reference to the foregoing example, the fluid tube 24 is placed near the skin 32, which may have a skin opening 34. The skin opening 34 and an insult source (outlet) 24a of the tube 24 simulate a human urethra and cooperate to direct the fluid 28 into the material 36, such as a diaper, which is placed about the skin 32 to be insulted with fluid 28. In this example, the fluid tube 24 (and skin opening 34 if provided) is aligned substantially with the heater hole 20.

As suggested with respect to FIG. 3 above, a fluid loading protocol is used to simulate a child's model urine load, which is described in greater detail under the following Exemplary Procedures section. It is to be understood that the outlet 24a and skin opening 34 can vary in size and number to simulate tear ducts, body cavities, perspiration pores, and similar openings. Additionally, various other fluid loading protocols can be applied to model infant urination, adult perspiration, menses, synthetic breast milk and blood such as bovine blood or other fluid excretions. For instance, an adult incontinence product insult may be 105 millimeters (ml) to 480 ml. The protocol for insulting 105 ml or 480 ml are as follows: 3 loadings of 35 ml, 45 seconds apart, at 6 ml/sec (105 ml total) and 3 loadings of 75 ml, 15 minutes apart at 8 ml/sec (total of 480 ml) for a large size product.

Although skin 32 is shown wrapped around the heater 18 in FIG. 4, it is to be understood that the skin 32 may be a small patch or square of skin 32 relative to the heater 18 as seen in FIG. 5. The small patch of skin 32 is placed at pre-selected distances from the heater hole 20 and outlet 24a. For example, research has shown that 6 cm is an advantageous distance from the insult source 24a to the skin 32. Using VITRO-SKIN™ as the skin 32, the inventors have found by placing the skin 32 at various locations on the arm 12, that fewer differences are detectable the closer the simulated skin 32 is placed to the insult source 24a. In other words, although distances of about zero cm to about 12 cm are feasible, TEWL measurements may undesirably vary or be difficult to differentiate when the skin 32 is too close to the insult source 24a and a surge area of the fluid 28.

It is to be noted that the VITRO-SKIN™ is sensitive to the environment under the material 36 when starting from a dry state (preconditioned at 40% RH). When the VITRO-SKIN™ becomes flooded or saturated with fluid 28, high TEWL readings reflect no product differences. It is to be noted that if the VITRO-SKIN™ is used without rinsing it, the TEWL values are stable for at least two uses. However, if the VITRO-SKIN™ is rinsed between uses and reconditioned to test humidity, the rinsed VITRO-SKIN™ is not re-usable. Important components such as glycerin may be washed off and negatively impact test results. Accordingly, at least if VITRO-SKIN™ is utilized as the skin 32, rinsing is not recommended.

With reference to FIG. 5, the heater 18 is shown attached to the arm 12 in a conventional manner such as by a hook and loop fastening system, tape or the like. The electrical connection 22b and fluid tube 24 are routed within the arm 12, which is hollow in this example, although one or both of the electrical connection 22b and fluid tube 24 can be routed externally if desired. The fluid tube 24 is then inserted through the fluid injection port 16 and heater hole 20 as described with respect to FIG. 4 above.

In operation, the material 36 (seen partially detached for clarity in FIG. 5) is securely wrapped about the arm 12 to at least partially cover the heater 18 and the skin 32. The fluid delivery device 26 delivers the fluid 28 through the tube opening 24a of the fluid tube 24 into the material 36 for TEWL or other evaluation as more particularly described in the following protocols and experiments.

I. Experiment Conducted on an Exemplary Embodiment of the Invention

Results derived from experiments conducted in accordance with one exemplary embodiment of the present invention are as follows. In the following hydration experiment, a diaper was tested on the evaluation apparatus 10 illustrated in FIG. 1.

In this experiment, a Step 3 Ultra-Trim® diaper was used as the material or diaper 36. The diaper 36 was attached about the heater 18 proximate the attachment area 14. The digital pump 26, capable of less than 1 cubic centimeter to over 500 cubic centimeters (see FIG. 1), was set to insult 60 cc/min of simulated physiological fluid or warmed saline 28 in 12 seconds. The digital pump 26 was further programmed to insult the diaper 36 with saline 28 three times. The diaper 36 was marked with a target measurement zone (not shown) 15.2 cm from a top front of the diaper 36 on its inside. The back of the diaper 36 was marked on its outside approximately 5 cm from the top. The target loading zone should be measured and marked 21.2 cm from the top front of the diaper 36. The target loading zone was lined up directly under the tube 24 on the under side of the arm 12 with the front of the diaper 36 at the top. The back of the diaper 36 back was wrapped around the arm 12 and securely taped, with the back of the diaper located on the top of the arm and folded to the inside at the 5 cm mark. The diaper 36 is insulted with the saline 28 three times and evaluated after 30–90 minutes.

Result: Upon first injection of the saline 28 into the diaper 36, the evaluation apparatus 10 was used successfully to measure the skin 32.

II. Experiment Conducted on another Exemplary Embodiment of the Invention

Exemplary Procedure

Results derived from experiments conducted in accordance with another exemplary embodiment of the present invention are as follows. In this experiment with particular reference to FIGS. 1 and 4, the following test procedure employed a diaper 36 tested on the mechanical arm 12:

1. Preheat the mechanical arm (12) to 95° F. before beginning.
2. Turn on the computer (38) and DermaLab® instrument (40). Warm up according to manufacturer's directions.
3. Turn on the fluid delivery device (26).
4. Calibrate the fluid delivery device (26) prior to use.
5. Measure and mark TEWL measurement zone 15.2 cm from the top inside edge of a Step 3 diaper (36).
6. Measure and mark Loading Zone—21.2 cm from the top inside edge of a Step 3 diaper (36).
7. Using an unused piece or patch (32) of simulated skin—for this experiment, a 5 cm×3.8 cm patch of VITRO-SKIN™ was used—place it securely on the side of the mechanical arm (12) using waterproof surgical tape. The VITRO-SKIN™ should be on the side facing the experimenter (rough side out), approximately 0.75 cm from the top of the heating element (not shown).
8. Place the diaper (36) on the arm (12) with the front waistband facing the experimenter. Align the TEWL measurement zone (15.2 cm) on the diaper (36) with the patch (32). The diaper (36) should be wrapped down and around the arm (12) with the back of the diaper (36) slightly folded. The front waistband wraps slightly over the back. Ensure that the loading tube (24) embedded in the arm (12) lines up with the loading zone on the diaper (36). The diaper (36) is secured on the arm (12) by masking tape. The tape is tightly wrapped around both ends of the diaper (36).
9. Use program 3S300T45 on the computer in the WIN-LIN software. Press start to begin the loading procedure. 60 milliliter/second (mls) of saline (28) should begin to flow into the diaper (36) at 300 cc/mm every 45 seconds, three times or a total load of 180 mls.
10. After the third and final insult, set and start a timer for 60 minutes.
11. After 60 minutes, open the diaper (36) and quickly remove the patch (32) from the arm (12) and place the patch (32) on a cosmetic sponge (not shown) for a TEWL measurement.
12. Record the TEWL measurement in a notebook, and save it to a Microsoft® Excel file.

Exemplary Results

The initial TEWL value for the patch (32) prior to use on the arm (12) was zero $g/m^2/hr$. The patch (32) was conditioned in a controlled laboratory setting at 72° Fahrenheit +/– 2° Fahrenheit, 40% RH +/– 5%. Typically, a baseline TEWL measurement is taken on human skin prior to conducting known Clinical Research Service (CRS) Adult Armband Testing. The baseline value is then subtracted from the final TEWL value for a trans-epidermal water loss measurement in units of $g/m^2/hr$. For this experiment, since the initial TEWL value was zero $g/m^2/hr$, no subtraction was necessary.

A strong correlation was shown between the CRS Armband Test versus this exemplary experiment ($R^2=0.958$). This indicates that using a mechanical apparatus as a screening tool for materials and components of products is effective and practical.

Moreover, in a small scale study two groups of diapers 36, each numbering ten diapers, were evaluated three weeks apart using the foregoing protocol with no significant differences detected between the two groups of diapers 36 from the same bag and lot number. The study therefore shows that the testing is repeatable with at least a 95% confidence level.

Based on the strong correlation between the CRS Armband Test and this mechanical experiment and its repeatability, the experiment can be used as a bench test for evaluating test equipment and pre-screening materials for skin dryness for use in final product testing. However, it is to be understood that the experiment may also be used to screen competitive products, perform other research and development, and the like and is not limited to the foregoing exemplary uses.

While preferred embodiments of the invention have been shown and described, those skilled in the art will recognize that other changes and modifications may be made to the foregoing embodiments without departing from the spirit and scope of the invention. For example, specific shapes of various elements of the illustrated embodiment may be altered to suit particular applications such as shaping the object 12 as a lower torso mannequin, an upper torso mannequin, a full body mannequin, a mannequin forearm, a mannequin hand, a mannequin foot, a mannequin head and various other portions of a human body. Also, it is to be noted that while the foregoing exemplary experiments used specific exemplary fluid insult protocols, various protocols ranging, for example, from between less than 1 cc/min to about 800 cc/min for 10–60 seconds at various intervals may be substituted to simulate various age groups and bodily excretions. It is intended to claim all such changes and modifications as fall within the scope of the appended claims and their equivalents.

That which is claimed is:

1. An apparatus for evaluating a material insulted with a fluid from a fluid delivery device, the apparatus comprising:
    an object having a port therethrough; and
    a heater having a hole therethrough with a substrate removably attached to the heater, the heater configured for attachment to the object and further configured to heat the substrate, a material disposable about the heater and the substrate, the port and the hole cooperably configured to pass a simulated bodily fluid into communication between the heater and the material proximate the substrate.

2. The apparatus as in claim 1, wherein the object is selected from the group consisting of a lower-torso mannequin, an upper-torso mannequin, a full-body mannequin, a mannequin forearm, a mannequin hand, a mannequin leg, a mannequin foot, a mannequin head, and combinations thereof.

3. The apparatus as in claim 1, further comprising a base configured for removable attachment to the object.

4. The apparatus as in claim 3, wherein the object is adjustable relative to the base.

5. The apparatus as in claim 1, wherein the object is formed of a substance selected from the group consisting of a plastic, an acetyl plastic, an acrylic plastic, an elastomeric material, a high density polyethelene, a polymer, a metal, a glass, a composite material and combinations thereof.

6. The apparatus as in claim 1, wherein the heater is formed of a flexible material selected from the group consisting of an elastomeric material, a rubber silicone, a neoprene and combinations thereof.

7. The apparatus as in claim 1, wherein the heater is configured to heat from between 70° F. to about 120° F. to heat the substrate to a normal human body temperature.

8. The apparatus as in claim 1, wherein the heater is configured to heat from between 92° F. to about 99° F. to heat the substrate to a normal human body temperature.

9. The apparatus as in claim 1, wherein the hole is from between about 0.25 inches to about 0.5 inches in circumference and further comprising a tubing embedded in the object in fluid communication with the fluid delivery device, the tubing having an opening terminating at the hole, the fluid delivery device and the tubing cooperably configured to insult a predetermined amount of the simulated bodily fluid through the hole.

10. The apparatus as in claim 1, wherein the substrate is selected from the group consisting of a medical grade collagen film, a collagen disposed in a sausage casing, a chamois, a cellulose film, a cultured skin substrate, a bioengineered skin, a living skin sample, a dead skin sample and combinations thereof.

11. The apparatus as in claim 1, wherein the substrate is disposed apart from the hole from between about 5 centimeters to about 10 centimeters.

12. The apparatus as in claim 1, further comprising the fluid delivery device, wherein the fluid delivery device is a pump in communication with a tubing disposed in the object, the tubing having an opening terminating at the hole, the pump and the tubing cooperably configured to insult a predetermined amount of the simulated bodily fluid through the hole.

13. The apparatus as in claim 1, further comprising the fluid delivery device, wherein the fluid delivery device is a computer controlled pump in communication with a tubing in the object, the tubing having an outlet thereon terminating proximate the hole, the computer controlled pump and the tubing cooperably configured to insult a predetermined amount of the simulated bodily fluid through the hole.

14. The apparatus as in claim 13, wherein the substrate defines an opening therein, the substrate opening and the tubing outlet cooperable to simulate an aperture selected from the group consisting of a tear duct, a urethra, a pore, a body cavity, and combinations thereof.

15. The apparatus as in claim 13, further comprising the tubing.

16. The apparatus as in claim 1, wherein the material is a absorbent article selected from the group consisting of disposable or non-disposable diapers, disposable or non-disposable adult incontinence products, disposable or non-disposable feminine products, nursing healthcare products, disposable or non-disposable child training pants, face masks, bandages, gloves and combinations thereof.

17. The apparatus as in claim 1, wherein the simulated bodily fluid is selected from the group consisting of water, saline, synthetic or natural menses, synthetic or natural urine, artificial or natural breast milk, synthetic or natural blood, 0.9% sodium chloride solution, colored solution, an exudate and combinations thereof.

18. The apparatus as in claim 1, further comprising a measuring device configured to measure a condition of the substrate by one of capacitance, conductance, electrical impedance, and TEWL.

19. The apparatus as in claim 18, wherein the condition is selected from the group consisting of dryness, wetness, temperature, and combinations thereof.

20. An apparatus for evaluating a material insulted with a fluid from a fluid delivery device, the apparatus comprising:
    an object having a fluid injection port and a heating surface, the fluid injection port configured to insult a simulated human fluid into a material; and
    a substrate removably attached to the heating surface, the heating surface configured to heat the substrate to a human skin temperature, the material disposable about the substrate and the fluid injection port.

21. The apparatus as in claim 20, wherein the object is formed of a silicone, a neoprene, a plastic, an acetyl plastic, an acrylic plastic, an elastomeric material, a high density polyethelene, a polymer, and combinations thereof.

22. The apparatus as in claim 20, further comprising a heater integral to the object and configured to heat the heating surface from between about 70° F. to about 120° F.

23. The apparatus as in claim 20, further comprising a heater integral to the object and configured to heat the heating surface from between about 92° F. to about 99° F.

24. The apparatus as in claim 20, wherein the material is an article selected from the group consisting of disposable or non-disposable diapers, disposable or non-disposable adult incontinence products, disposable or non-disposable feminine products, nursing healthcare products, disposable or non-disposable child training pants, face masks, bandages, gloves and combinations thereof.

25. The apparatus as in claim 20, wherein the simulated human fluid is selected from the group consisting of water, saline, synthetic or natural menses, synthetic or natural urine, artificial or natural breast milk, synthetic or natural blood, 0.9% sodium chloride solution, colored solution, exudate and combinations thereof.

26. The apparatus as in claim 20, further comprising the fluid delivery device, wherein the fluid delivery device is a pump in communication with an embedded tubing within the object, the embedded tubing having an opening terminating at the fluid injection port, the pump and the embedded tubing cooperably configured to insult a predetermined amount of the simulated human fluid through the fluid injection port.

27. The apparatus as in claim 20, wherein the object is selected from the group consisting of a lower-torso mannequin, an upper-torso mannequin, a full-body mannequin, a mannequin forearm, a mannequin hand, a mannequin leg, a mannequin foot, a mannequin head, and combinations thereof.

28. The apparatus as in claim 20, further comprising a measuring device configured to measure a condition of the substrate.

29. The apparatus as in claim 28, wherein the measuring device measures the condition of the substrate by one of capacitance, conductance, electrical impedance, and TEWL.

30. The apparatus as in claim 28, wherein the measuring device is configured to record the condition of the substrate.

31. The apparatus as in claim 28, further comprising a monitor in electrical communication with the measuring device, the monitor configured to display the condition of the substrate.

* * * * *